United States Patent
Gross et al.

(10) Patent No.: US 10,282,800 B2
(45) Date of Patent: May 7, 2019

(54) SYSTEM AND METHOD FOR PROVIDING MEDICAL CAREGIVER AND EQUIPMENT MANAGEMENT PATIENT CARE

(75) Inventors: Brian David Gross, North Andover, MA (US); John Louis Barga, Newton, MA (US); Martin Bufe, Ebersbach (DE); Elizabeth Zengo, Hudson, NH (US); Andreas Pirrung, Nufringen (DE); Guenter Gegner, Tuebingen (DE); Wilhelm Meier, Herrenberg (DE)

(73) Assignee: Koninklijke Philips N.V., Eindhoven (NL)

( * ) Notice: Subject to any disclaimer, the term of this patent is extended or adjusted under 35 U.S.C. 154(b) by 1063 days.

(21) Appl. No.: 13/995,326

(22) PCT Filed: Dec. 16, 2011

(86) PCT No.: PCT/IB2011/055732
§ 371 (c)(1),
(2), (4) Date: Jun. 18, 2013

(87) PCT Pub. No.: WO2013/085791
PCT Pub. Date: Jun. 28, 2012

(65) Prior Publication Data
US 2013/0297350 A1 Nov. 7, 2013

Related U.S. Application Data

(60) Provisional application No. 61/426,001, filed on Dec. 22, 2010.

(51) Int. Cl.
*G06F 19/00* (2018.01)
*G06Q 50/24* (2012.01)
*G16H 40/20* (2018.01)

(52) U.S. Cl.
CPC ............. *G06Q 50/24* (2013.01); *G06F 19/00* (2013.01); *G06F 19/3418* (2013.01); *G16H 40/20* (2018.01)

(58) Field of Classification Search
CPC ....................................................... G06H 40/20
(Continued)

(56) References Cited

U.S. PATENT DOCUMENTS 7,541,935 B2   6/2009  Dring et al.
7,698,002 B2   4/2010  Music et al.
(Continued)

FOREIGN PATENT DOCUMENTS

JP  2009219867 A   10/2009
WO  2006051464 A1   5/2006
(Continued)

OTHER PUBLICATIONS

Mussi, J., et al.; iHE; IHE IT Infrastructure; XDS Patient Identity Management White Paper; Draft for Public Comment; Aug. 10, 2010. 26 pages.

Primary Examiner — Hiep V Nguyen
Assistant Examiner — Trang T Nguyen

(57) ABSTRACT

A medical device and caretaking management system (10) includes a plurality of medical devices (14) that transmit equipment data and patient data. A central or distributed monitoring system (12) receives the equipment data and patient data from the plurality of medical devices, derives an acuity for each of the patients, and assigns caregivers and equipment based on the derived acuity for display on a display device (26).

19 Claims, 4 Drawing Sheets

(58) Field of Classification Search
USPC .......................................................... 705/3
See application file for complete search history.

(56) References Cited

U.S. PATENT DOCUMENTS

| | | | |
|---|---|---|---|
| 2003/0212379 A1 | 11/2003 | Bylund et al. | |
| 2005/0075904 A1 | 4/2005 | Wager et al. | |
| 2006/0047538 A1* | 3/2006 | Condurso | G06F 19/3468 705/3 |
| 2006/0074740 A1* | 4/2006 | Garcia | G06Q 10/06 705/7.14 |
| 2006/0161456 A1* | 7/2006 | Baker | G06F 19/327 705/2 |
| 2006/0184943 A1* | 8/2006 | DelMonego | G06Q 10/06 718/100 |
| 2006/0265186 A1* | 11/2006 | Holland | G06F 19/3468 702/182 |
| 2006/0287906 A1* | 12/2006 | McGillin | G06Q 10/06 705/7.14 |
| 2007/0083344 A1* | 4/2007 | Holland | G06F 19/3468 702/182 |
| 2007/0288263 A1* | 12/2007 | Rodgers | 705/2 |
| 2008/0126126 A1* | 5/2008 | Ballai | G06F 19/327 705/2 |
| 2008/0214904 A1* | 9/2008 | Saeed | A61B 5/0006 600/301 |
| 2008/0215627 A1* | 9/2008 | Higgins | G06F 19/322 |
| 2009/0055215 A1* | 2/2009 | Giraldo | G06F 19/327 705/2 |
| 2009/0205042 A1 | 8/2009 | Zhou et al. | |
| 2009/0205091 A1 | 8/2009 | Haaheim | |
| 2009/0306542 A1 | 12/2009 | Azer et al. | |
| 2009/0319292 A1 | 12/2009 | Warner et al. | |
| 2009/0327102 A1* | 12/2009 | Maniar | G06F 19/327 705/28 |
| 2010/0239682 A1* | 9/2010 | Andremont | A61K 9/1652 424/497 |
| 2010/0305966 A1* | 12/2010 | Coulter | G06Q 10/04 705/2 |
| 2011/0169644 A1* | 7/2011 | Muhsin | G06F 17/30516 340/573.1 |
| 2012/0253836 A1* | 10/2012 | Nolte | G06Q 50/22 705/2 |

FOREIGN PATENT DOCUMENTS

| | | |
|---|---|---|
| WO | 2007084807 A1 | 7/2007 |
| WO | 2009083840 A1 | 7/2009 |

* cited by examiner

FIG. 3

Caregiver assignments

Unit: Unit 12
Charge Nurse: Lee, Kathy

Caregivers — 202

| Name | Paging device | Role(s) |
|---|---|---|
| Stein, John | 2222 | Care tech |
| Goss, Brian | | Care tech |
| Lee, Kathy | 1111 | Nurse (Charge nurse) |
| Reid, Scott | 3333 | Nurse |
| Smith, Joe | 4444 | CDS nurse |
| Warren, Brian | | Nurse |
| Welsh, Kathleen | | Nurse, CDS nurse, (C |
| Zengo, Beth | | Charge nurse |

204  206  208

Quality statistics summary — 218
- Number of patients: 8 — 220, 222
- Number of assigned caregivers: 3
- Average EWS score: 5 — 224, 226
- Number of deterioration notifications: 11

Paging Device:

Bed Assignments — 210

| Location | Patient name | EWS | Nurse | Care tech | CDS Nurse |
|---|---|---|---|---|---|
| Bed 1 | Not admitted | | Lee, Kathy | Stein, John | |
| Bed 2 | Not admitted | | Reid, Scott | Stein, John | |
| Bed 3 | Doe, Jane | 3 | Lee, Kathy | Stein, John | Welsh, Kathleen |
| Bed 4 | Not admitted | | Reid, Scott | Stein, John | |
| Bed 5 | Doe, John | 7 | Smith, Joe (Welsh, Kathleen) | | Welsh, Kathleen |
| Bed 6 | Leed, Erica | | Reed, Scott | | |
| Bed 7 | Clinton | → | Smith, Joe (Welsh, Kathleen) | | Welsh, Kathleen |
| Bed 8 | Brown, Sue | | | | |

212  214  216  230

Clear assignments
Delegation ...
Caregiver setup ... — 232
Paging ... — 228
Quality statistics ...
Re-Activate EWS Deterioration notification — 234

Apply  Cancel

200

42, 44

SYSTEM AND METHOD FOR PROVIDING MEDICAL CAREGIVER AND EQUIPMENT MANAGEMENT PATIENT CARE

CROSS REFERENCE TO RELATED APPLICATIONS

This application is a national filing of PCI application Serial No. PCT/IB2011/055732, filed Dec. 16, 2011, published as WO 2012/085791 A1 on Jun. 28, 2012, which claims the benefit of U.S. provisional application Ser. No. 61/426,001 filed Dec. 22, 2010, which is incorporated herein by reference.

The present application relates to central or distributed monitoring stations for intelligent medical equipment and caregiver management. It finds particular application in utilizing equipment setting and patient data to drive acuity based caregiver assignments, equipment assignments, and system settings and will be described with particular reference thereto.

Presently, caregivers and medical equipment are manually assigned to given patients on separate systems. In one system, caregivers are typically assigned to a patient by a caregiver manager on a regular basis (e.g. per weekend, day, night, shift, and the like) based on various factors including the availability of nurses, qualifications of available caregivers, the number of available beds in the unit, the current utilization of the beds in the unit, the existing responsibilities of the caregivers, and the like. In another system, caregivers manually enter or select a patient ID for each piece of medical equipment used for a given patient. With the advent of smaller and smarter medical equipment and larger medical facilities that employ a large number of caregivers, the burden of entering and removing patient IDs from equipment and assigning caregivers has dramatically increased.

The present application provides a new and improved system and method for medical equipment and caregiver management which overcomes the above-referenced problems and others.

In accordance with one aspect, a medical device and caretaking management system is provided. A plurality of medical devices transmit equipment data and patient data. A central or distributed monitoring central or distributed monitoring station receives the equipment data and patient data from the plurality of medical devices and assigns caregivers based on the equipment data and patient data.

In accordance with another aspect, a method for managing and archiving medical devices and caregivers is provided. The method comprising receiving patient data and equipment data from a plurality of medical devices, the patient data and equipment data being transmitted from one or more medical devices assigned to each of a plurality of patients, deriving an acuity for each of a plurality of patients based on the patient data and equipment data, and making and dynamically changing caregiver assignments, equipment settings, and alarms based on the derived acuities.

In accordance with another aspect, a system is provided comprising one or more processors programmed to derive an acuity for each of a plurality of patients based on monitored data received from, equipment assigned to, and settings of the equipment assigned to each patient. Based on the derived acuities making and dynamically changing caregiver assignments, equipment settings, and alerts. The system also including one or more display devices on which the caregiver assignments, the equipment settings, and the alerts are displayed.

One advantage resides in the intuitive, automatic, and fast method to maintain patient IDs as devices are moved between patient and as patients are moved between care units.

Another advantage resides in improved caregiver workflow and patient care.

Another advantage resides in improved equipment assignment and settings adjustments.

Another advantage resides in tracking and detecting equipment or caregiver related nosocomial infections.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 3 illustrates a user interface of an administration manager of a central or distributed monitoring station in accordance with the present application.

Figure 1:
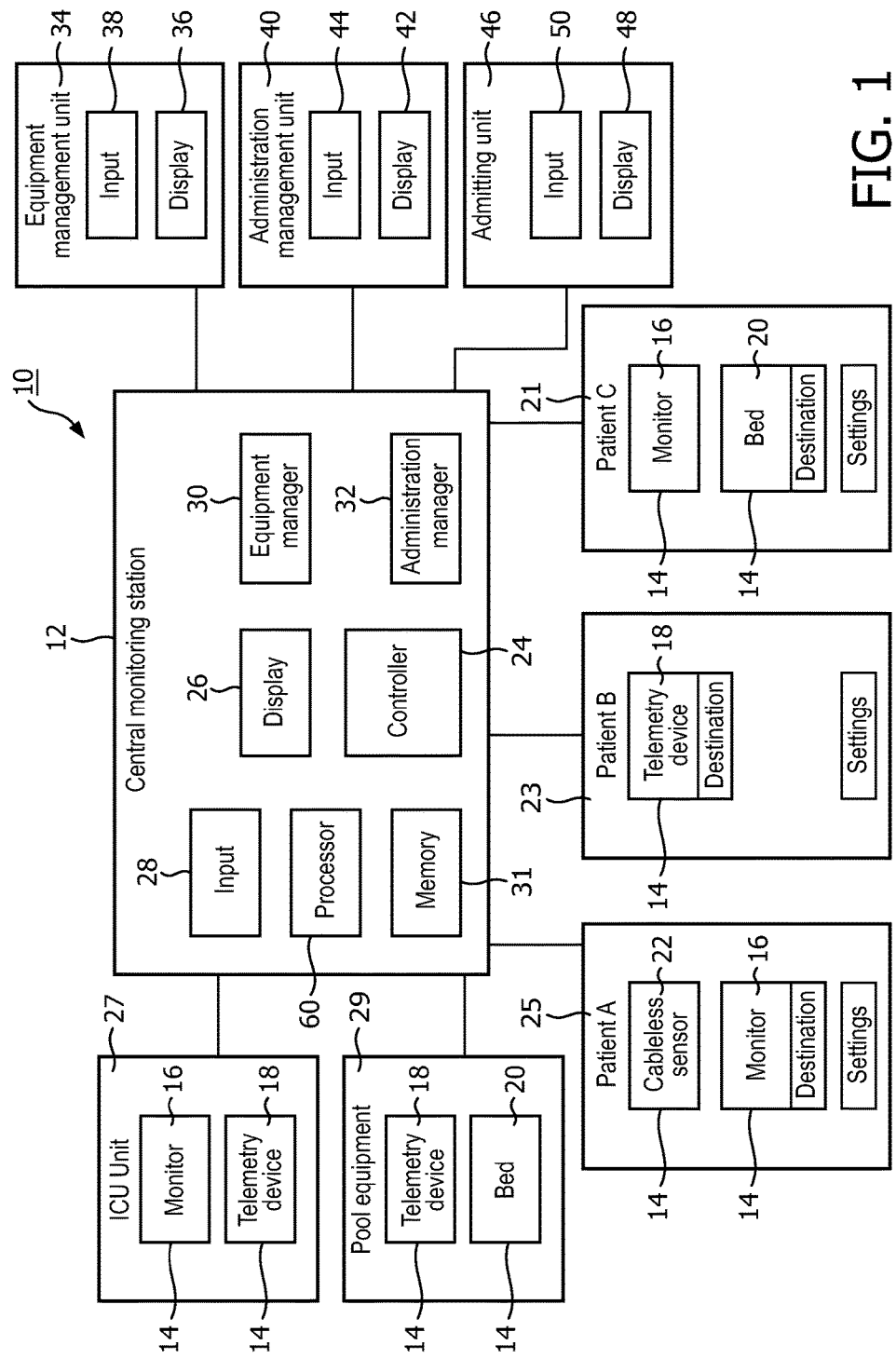
FIG. 1 is a diagrammatic illustration of a centralized equipment and caretaking management system in accordance with the present application.

With reference to FIG. 1, a centralized equipment and caregiver management system 10 includes a central or distributed monitoring station 12 for receiving equipment and patient data from a plurality of medical devices or equipment 14. The central or distributed monitoring station 10 drives acuity based (vital signs and Clinical Decision System (CDS) information) caregiver assignment, equipment assignment, system settings and the like. For example, the central or distributed monitoring station 12 may receive equipment data and patient data for a given patient relating to the type of equipment associated with the patient, the number of monitoring devices monitoring the patient, frequency of patient alarms or CDS events such as Early Warning System (EWS) severity, deterioration state, sepsis resuscitation, ACS therapy, and the like), the nature of the physiological condition of the patient, the location and destination of a patient, and the like to calculate the acuity and caregiver and equipment assignments for the patient. The medical devices 14 include multi-functional patient monitor devices (PMD) 16, telemetric monitoring devices 18, cableless sensors 22 and the like that monitor patients by various medical monitoring devices or sensors. The medical devices 14 measure physiological parameters of the patient continuously or at selectable intervals, on request or at predetermined times as a results of another CDS application and generate patient data, alarms, indicative thereof. It is should be appreciated that that medical devices 14 also include patient beds 20, oxygen tanks, portable ventilators, defibrillators, transport monitors, portable suctions, IV stands, and other equipment. The equipment can have various settings which control the services or level of assistance performed by the equipment. Which equipment is associated with each patients and the settings (e.g. IV drip rate, oxygen delivery cycles, etc), like the monitored data are also indicative of patient acuity. Other factors which effect acuity include patient (bed) location and destination of the patient is to be moved or is in transit. It is also contemplated that PMDs 16, other medical devices 14, and/or processors connected via a hospital network drive the acuity based caregiver assignment, equipment assignment, system settings and the like.

To enable management of the medical devices 14 and caregivers, each medical device 14 has associated device attributes that are transmitted as equipment data to and stored in the central or distributed monitoring station 12. The device attributes relate to the identification of the device, patient assignment of the device, usage of the device, state of the device, a device group, settings of the device, and a device pool. The identification attribute includes a unique device ID, a patient ID, and the like. The device ID uniquely represents the device 14 in the system 10 and contains a system interpretable label (GUID, MAC address, serial number, and the like) and a user readable label (equipment label, asset number, and the like). The patient ID uniquely represents a single human subject across a single care encounter or a lifetime and contains a system interpretable label (GUID and the like) and a user readable attribute (serial number, name, encounter number, record number, social security number, and the like). The patient ID is used to assign acquired patient data to the proper patient and synchronize patient setting and stored data in medical device 14. The patient identification includes a patient name, a patient identification, gender, date of birth, and the like. The usage attribute includes an indication of the use of the medical device. For example, the usage attribute includes a stationary status for medical devices 14 that are permanently located at a particular location, a portable status for medical devices 14 that are used as stationary equipment or transport equipment, a transport status for medical devices 14 that are used for transport. A state of the device attribute includes: (a) a free state when the medical device 14 is not assigned to a patient or the medical device 14 is in a default state, (b) an associated state when the medical device 14 is assigned to a patient, (c) a used state when the medical device 14 is detecting either physiological data or receiving setting changes, (d) an unused state when the medical device 14 has a default setting and no valid physiological signals are detected, (e) an orphan state when the medical device 14 does not have a system or host monitor connection, (f) a connected state when the medical device 14 has a system connection or a connection to a host monitor or waits for data for a (logically) connected device in a not always connected environment, and the like. The device group attribute includes an equipment group to which the medical device 14 is assigned. As illustrated, the medical devices 14 are assignable to a particular patient 21, assignable to a pool of free equipment and used for a patient, assignable to a bed 23 where all equipment assigned to the bed will automatically be used for the patient assigned the bed, able to be locked to the bed 25 where the medical device 14 is locked and always associated with the bed, assignable to a monitor or telemetry device where all the medical devices 14 connected via an open standard or proprietary short range radio (Bluetooth, Zigbee, Short Range Radio, and the like) are assigned to a group, assignable to a care unit 27 such as the ER, ICU, and the like. The device pool attribute defines the device pool 29 assigned the device. For example, when a medical device is shared between various units and the device pool defines the boundaries to represent ownership of the medical device 14 such that medical device 14 can be return to the proper owner after use.

In one embodiment, the medical devices 14 transmit the equipment and patient data via the hospital network to a controller 24 of the central or distributed monitoring station 12 wherein the equipment and patient data is displayed on a display 26 and stored in memory 31. The controller 24 of the central or distributed monitoring station 12 controls the display 26 to display the equipment and patient data received from the medical device 14 in corresponding display 26. The central or distributed monitoring station 12 also includes an input device 28 that allows the user, such a caregiver to view, manipulate, modify, and/or interact with the equipment and patient data on the display 26. The input device 28 can be a separate component or integrated into the display 20 such as with a touch screen monitor. It should be appreciated that equipment data can be input in the central or distributed monitoring station 12 by the input device 28 and stored in the memory of the central or distributed monitoring station 12. It is also contemplated that PMDs 16, other medical devices 14, and/or processors connected via the hospital network receive the equipment and patient data transmitted by the medical devices 14.

The central or distributed monitoring station 12 also includes an equipment manager 30 for managing and maintaining the medical devices 14 and patient IDs as they are moved between patients and as patients are moved between care units. The equipment manager 30 determines and stores the medical device 14 to patient relationships. The stored medical devices 14 to patient relationships are displayed in the display 26 of the central or distributed monitoring station 12. The equipment manger 30 also stores or archives historical data relating to past assignment of medical device 30 assignments such that a clinician can determine the pervious assignment of the data to determine if a patient conflict exists. The central or distributed monitoring station 12 can also display a list of a particular patient's associated equipment based on the medical device 14 to patient relationships. The medical device 14 to patient relationship can be established in multiple ways including the user entering the patient ID or selecting the patient ID from the patient list at the medical device 14, the medical device 14 or central or distributed monitoring station 12 reading patient information from a barcode or RFID, by entering the patient ID or selecting the patient ID from the patient list at the central or distributed monitoring station 10 for a particular medical device 14, by adding a medical device 14 for an existing patient (manually selected or caused by transfer), and the like. The medical device 14 to patient relationship can be terminated by ending the patient case, transferring the patient without the medical device 14, using the medical device 14 for a new patient, manually removing the medical device 14, automatic freeing the medical device 14 when not used for a specific time period. When the medical device 14 to patient relationship is terminated the patient identification and patient data are cleared in the medical device 14 and the settings are reset to defaults. Some devices are not reassignable until after the device has undergone decontamination processing, e.g. been assigned to and relocated from a decontamination unit. It is also contemplated that the operation of the equipment manager 30 can be performed at or distributed among the PMDs 16, other medical devices 14, and/or processors connected via the hospital network. For example, the PMDs 16, other medical devices 14, and/or processors collectively or individually can determine and store the medical device 14 to patient relationship, display the medical device 14 to patient relationships, establish or modify the medical device 14 to patient relationships, and the like.

The central or distributed monitoring station 12 and the equipment manager 30 also enable the medical devices 14 to be in communication with each. The central or distributed monitoring station 12 and equipment manager 30 allow the medical devices 14 to control and communicate with each other to determine the patient IDs to manage medical devices 14. The medical devices 14 can determine whether other devices are monitoring a particular patient ID and the location of those medical devices 14 in order to further refine the medical device 14 to patient relationship. The central or distributed monitoring station 12, PMDs 16, other medical devices 14, and/or processors connected via the hospital network can also determine what patient IDs are being monitored by the system and then allow other medical devices to see that device assignment.

When the user adds a medical device 14 for a patient via central or distributed monitoring station 12, the equipment manager 30 determines the medical device 14 to patient relationship based on a plurality of rules and guidelines. The medical devices 14 to patient relationships are determined from the previous current and previous assignments for each of medical device 30. If the added medical device 14 is free or not assigned to a patient, the new medical device 14 is used for the current patient (if any). If a patient is assigned to the new medical device 14 and other medical devices and equipment 14 are free such as a bed or monitor, all of the medical devices 14 are assigned to the patient. If different patients are assigned to both new and old medical devices 14, a patient conflict is detected and resolved which will described below. When the medical device 14 is free and assigned to a current patient, the patient information and patient demographics are set for the device and the device is added to the list of the patient's associated equipment. If a medical device 14 is orphan or monitoring a patient but is not assigned to a particular patient, the central or distributed monitoring station 12 and equipment manager 30 properly assigns the orphan medical device 14 to that patient. If the orphan medical device is monitoring the same patient and the user wishes to assign the device to the patient, the equipment manager 30 will automatically connect and add the medical device 14 to the patient list. If the orphan medical device is monitoring a different patient, the equipment manager 30 will compare the patient identification and check for patient conflicts. If there is a patient conflict, the equipment manager 30 will resolve the conflict as described below.

The user may also remove medical devices 14 assigned to a patient via the central or distributed monitoring station 10. The user may remove medical devices 14 when the device is no longer required. The user may remove a single device or a group of devices. When a medical device 14 is unassigned from the patient the medical device 14 will prepare the medical device 14 for the next patient, for example by freeing the device or clearing the patient identification and all other patient data of the old patient, creating a new internal patient number, setting and configuring the medical device 14 as specified in the default profile, and the like. Medical devices 14 can also be automatically unassigned from a patient by exceeding a specified power-off or standby period or period without receiving valid physiological data from the patient.

The central or distributed monitoring station 10 and the equipment manager 30 also manage and maintain the medical device 14 to patient relationships of transferred medical devices 14 and patients. If a patient is transferred to another unit or bed, the equipment manager 30 determine whether the medical device 13 was kept or unassigned from the patient. If the medical device is kept by the patient, the medical device 14 is generally transferred with the patient and therefore remains assigned to the patient unless the equipment cannot be used in the destination unit. If the medical device 14 assigned to the patient is no longer required, the user manually removes the medical device 14 or relies on the equipment manager to unassign the medical device 14 when the device is not used for a specific time. If the medical devices 14 are assigned to the bed or unit, when the patient is transferred to another bed or unit, the bed and any medical device 14 assigned or locked to the bed are freed. The user may manually transfer the patient to another bed or unit or transfer a patient from another bed or unit by selecting the patient at the destination monitor or bed from the patient list or by inputting the transfer into the central or distributed monitoring station 12, the equipment manger 30, or the medical device 14 itself. The central or distributed monitoring station 12 and the equipment manager 30 may automatically determine a patient transfer. When a patient is moved with the assigned medical devices 14, the central or distributed monitoring station 12 and equipment manager 30 can determine that the medical devices was transferred to a new bed or unit. For example, after plugging the medical device 14 into a new location the equipment manager 30 determines which medical devices 14 are assigned to that particular patient and transfers the equipment and patient data to the new bed or unit. If the medical device 14 becomes unconnected from the hospital network, the equipment manager 30 re-synchronizes the medical device 14 upon connected to automatically update the patient to medical device 14 relationship.

When medical devices 14 are connected, any patient management action executed affects all of the assigned medical devices 14 and therefore the patient identification is updated and kept identical in all medical devices 14. When a medical device 14 is freed, the patient identification in this device is cleared. If the patient identification or equipment assignment is changed while the device is not connected, a patient conflict is detected when the device is reconnected. Patient conflicts occur anytime a new patient identification is detected to an already assigned medical device 14 or the patient identification is different from expected assignment of the medical device 14. For example, patient conflicts exist when a patient is transferred with medical devices 14, e.g. patient is transferred and plugged to a monitor currently used for another patient, medical devices 14 that are currently used for another patient are added, a patient identification or equipment is changed offline, and the like. When a medical device 14 is connected to the central or distributed monitoring station 12, the patient identification of the connected device is compared with any previous assigned of the medical device 14 to determine if any conflicts exist. Patient conflicts are resolved by the central or distributed monitoring station 12 and the equipment manager 30. A patient conflict exits when the patient identifications being assigned to a medical device 14 is compared to an already assigned patient identification and the patient identifications are different. If there is no patient conflict, the patient data of the newly assigned and previous assigned patient are simply merged. If there is a conflict, the user is notified by a prompt. In some cases, the equipment manager automatically resolves the conflict by unassigning a previously assigned patient, assigning the patient to another free medical device, and the like. The equipment manager or medical device can also ask a specific question to the user e.g. "Continue with arriving patient?" in order to resolve the conflict.

The equipment manager 30 may also restrict use of the medical devices 14 to a single to multiple care units. Centrally managed medical devices 14 can be setup to be either used in a single unit or be part of an equipment pool and thus be used in multiple units. Medical devices 14 which are not supposed to be used in a unit do not appear in the equipment list of this unit and cannot be added. If the user however physically moves, for example plugs or telemetry device to a monitor in another unit, a unit conflict may occur. If supported by the monitor the medical device 14 can be used at the other monitor but the user is notified by a status text "Equipment owned by other unit—please return". This allows transfer of a patient with such medical device 14 to another bed and enforcement of the ownership of the medical device 14. The central or distributed monitoring station 12 and the equipment manager 30 can temporally assign the medical device 14 to a unit that it is not assigned to for use. After the unit is done using the temporally assigned medical device 14 the central or distributed monitoring station 12 can send a message to return equipment to proper unit.

The central or distributed monitoring station 12 also includes an administration manager 32 for managing and assigning caregivers to patients and units. The administration manager 32 assesses acuity of the patients among whom caregivers are to be distributed. Acuity is determined by various factors such as monitor data and alarms from the patient, equipment assigned to the patient, settings of the equipment, location or destination of the patient, and the like. The administration manager 32 maintains and stores the assignments of the caregivers to patients based on patient acuities credentials of caregivers and the like. The assignments can dynamically change with changes in patient acuity, adding or removing patients, and the like. The central or distributed monitoring station 12 can also display a list of a caregiver assignments based on the caregiver to patient relationships. The caregiver to patient relation can be established in multiple ways including an administration manager entering the patient ID or selecting the patient ID from the patient list at the central or distributed monitoring station 12 for each caregiver, and the like. The central or distributed monitoring station 12 and administration manager 32 changes the caregiver assignments dynamically based on the types of equipment being used for each patient, the number of monitoring devices assigned to each patient, the frequency of alarms or events, the natures of the physiological data collected from the patient, and the like. The administration manager 32 also evaluates the caregiver assignment from previous shifts to determine the efficiency of the caregiver assignments. For example, the administration manager 32 will determine if too many or few caregivers were assigned to a certain care unit in the previous shift. The administration manager uses this information to optimize the caregiver assignment to increase caregiver workflow and the quality of patient care.

The central or distributed monitoring station 12 also evaluates the physiological data from each patient for changes in acuity. For example, the evaluation checks for alarms, whether each measured parameter is approaching threshold values, whether a trend of any parameter is approaching a threshold, whether any parameter lacks stability or fluctuates too much, combinations of parameters are approaching a threshold, and other indicators that a patient needs more or less medical monitoring and therefore generates additional CDS information for assessment of the current patient state or a CDS patient status change, for example a EWS risk band change, a sepsis status change, triage status change, and the like. The thresholds include values exceeding a limit based on time, severity, escalation, or the like. In response to an alarm condition or an event, the administration manager 32 can dynamically change the assignment of caregivers to optimize the assignment of caregivers.

Specifically, the administration manager 32 determines caregiver assignments based on patient acuity and status and caretaking quality. The patient acuity includes the current and previous status and state of the patients, CDS Protocol information (e.g. Sepsis, Triage Acuity, EWS, ACS, ventilator weaning status, operation room procedure plan status, and the like). Caretaking quality includes the number of patients, number of assigned caregivers, average patient status, and number of alarm conditions or events. The administration manager 32 utilizes the patient status and the caregiver quality to dynamically change the caregiver assignments. For example, the administration manger 32 determines the number of patients/percentage of patients having an alarm conditions or events to change number of caregivers added to the percentage to determine if adding caregivers to a shift ratio reduces the trend of alarm conditions and events or EWS (CDS) deterioration (patient status change) is directed and causes the system to automatically add or remove a caregiver.

The administration manager 32 also determines and stores the location of caregivers and their assigned patients and/or beds. The administration manager 32 utilizes this information for communicating with caregivers during alarm conditions and events. During an alarm condition or event, the administration manager 32 can send a message informing the assigned caregiver of the alarm condition or event to all of the bed or monitors assigned to the caregiver's patients. To enable this type of communication, the administration manager 32 determines all the patients assigned to the particular caregiver and communicates with the equipment manager 30 to determine all the medical devices 14 assigned to those patients. For example, if a patient assigned to a caregiver is experiencing an alarm condition, the administration manager 32 will transmit an alert to all the beds and monitors that the caregiver is attending to ensure that the caregiver receives the message. The central or distributed monitoring station 12, administration manager 32, and the equipment manager 30 also track and detect equipment and caregiver related nosocomial infections from the equipment and caregiver assignments. For example, the central or distributed monitoring station 12, administration manager 32, and the equipment manager 30 can track any equipment or caregiver assigned to a patient that acquires an infection in the first 48 hours or more after hospital admission or within 30 days after discharge.

Optionally, an equipment management unit 34 manages and maintains the medical devices 14 and patient IDs as they are moved between patients and as patients are moved between care units. For example, the equipment management unit 34 also stores the medical device 14 to patient relationships and displays the relationships in a display 36, establishes the medical device 14 to patient relationships through an input device 38, resolves patient conflicts, and restricts the use of the medical devices as described above. The equipment manager 32 also recommends equipment assignments, reassignment, setting adjustments, and the like based on patient acuity. An administration management unit 40 may also manage and assign caregivers to patients and units, evaluate patient status and caretaking quality, and communication to caregivers as described above. The administration management unit 40 also includes a display 42 to display the caregiver assignments and an input device 44 to input the caretaking assignments. An admitting unit 46 may also manage the addition, removal, and the transfer of patients. The admitting unit includes a display 48 to display the patient locations and an input device 50 to add, remove, or transfer patients.

The central or distributed monitoring station 12 also assigns caregivers to patients, equipment to patients and patient acuity based on aforementioned medical device data content, equipment assignments, equipment settings, location, destination, and the like to modify the caregiver assignments, alert distribution settings, and equipment settings or behaviors. The types of equipment (monitor, thermal cooling, vent, IV pumps, meds administered), the number of devices, frequency of alarms, events, and measurement modes (spot check or continuous), the application state in use (EWS severity or deterioration state, sepsis resuscitation, ACS therapy . . . ), determine the acuity of the patient and the logical bounds of patient to caregiver assignment, alert distribution, and ultimately equipment settings. The central or distributed monitoring station 12 utilizes knowledge of patient location and destination to derive appropriate care team persistence or changes. The central or distributed monitoring station 12 also utilizes acuity as detected above to change the medical device settings and alarm/advisory distribution behaviors. For example, change the mode from spot check to continuous mode, or change from advisory mode (e.g. EWS deterioration notification) only to combined advisory and alarming mode, or escalate (workflow) advisories to physiological alarms, or from 1 hour measurement period to 1 minute measurement, or send only critical events and alarms, to send limit events and alarm, or to expand the alert distribution to other caregivers based on the acuity change detected.

The central or distributed monitoring station 21, equipment management unit 34, administration management unit 40, and the admitting unit 46 include at least one processor 60, for example a microprocessor or other software controlled device configured to execute management software for performing the operations described in further detail below. Typically, the management software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

Figure 2:
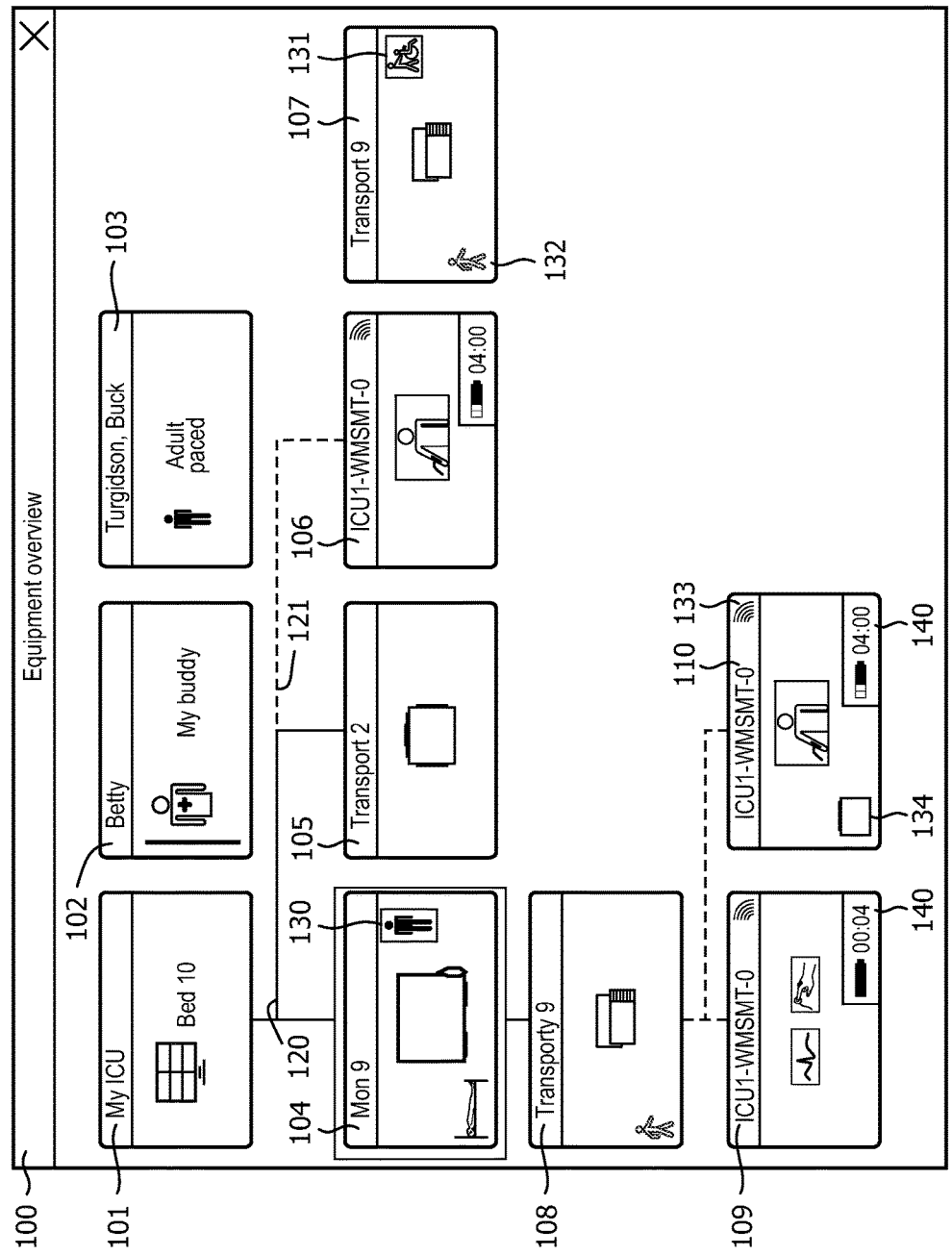
FIG. 2 illustrates a user interface of an equipment manager of a central or distributed monitoring station in accordance with the present application.

FIG. 2 illustrates a user interface 100 of the equipment manager 30 of the central or distributed monitoring station 12 and PMDs 16, medical devices 12, and other points of care. The equipment manager user interface 100 shows the assigned and connected equipment for a current patient and provides access to the patient and equipment management user actions. It is also contemplated that the user interface 100 can be displayed on an assignment medical device 14. The user interface 100 includes a central information sector 101 that includes the assigned bed and unit. The user interface 100 also includes a caregiver status 102 to indicate the status of the assigned caretaker. A patient identification icon 104 displays the patient identification, category, and paced mode. The user interface 100 also includes an icon 104 to indicate a bedside monitor assigned to a bed, an icon 105 to indicate a transport module is assigned to the patient, an icon 106 to indicate a cableless SpO2 measurement with direct central connection, an icon 107 to indicate a measurement server transferred with patient without connectivity, an icon 108 to indicate a measurement server transferred with patient connected to bedside monitor, an icon 109 to indicate a telemetry device connected to monitor, an icon 110 to indicate a cableless NBP measurement connected to monitor, and the like. The user interface 100 also displays the current connectivity of the assigned medical devices, such as a ITS or LAN wireless connection, a cable or wired connection, a wireless short range radio connection, and the like. The user interface 100 includes a wired connectivity symbol 120, a wireless connectivity symbol 121, a wireless connection quality symbol 133 and the like. A patient conflict symbol 130 indicates equipment having a patient conflict situation. A transfer status symbol 131 indicates equipment that is in the process of being transferred. Symbol 132 indicates that a specific piece of equipment is assigned to a patient and symbol 143 indicates that a specific piece of equipment is assigned to a monitor. The user interface 100 also includes battery symbols to indicate the battery status and remaining battery time 140 and a low battery status 141. It is also contemplated that the user interface control allow access to the relevant function of the system such as adding equipment, removing equipment, assigning a caregiver, discharging a patient, resolving a patient conflict, and the like.

Figure 4:
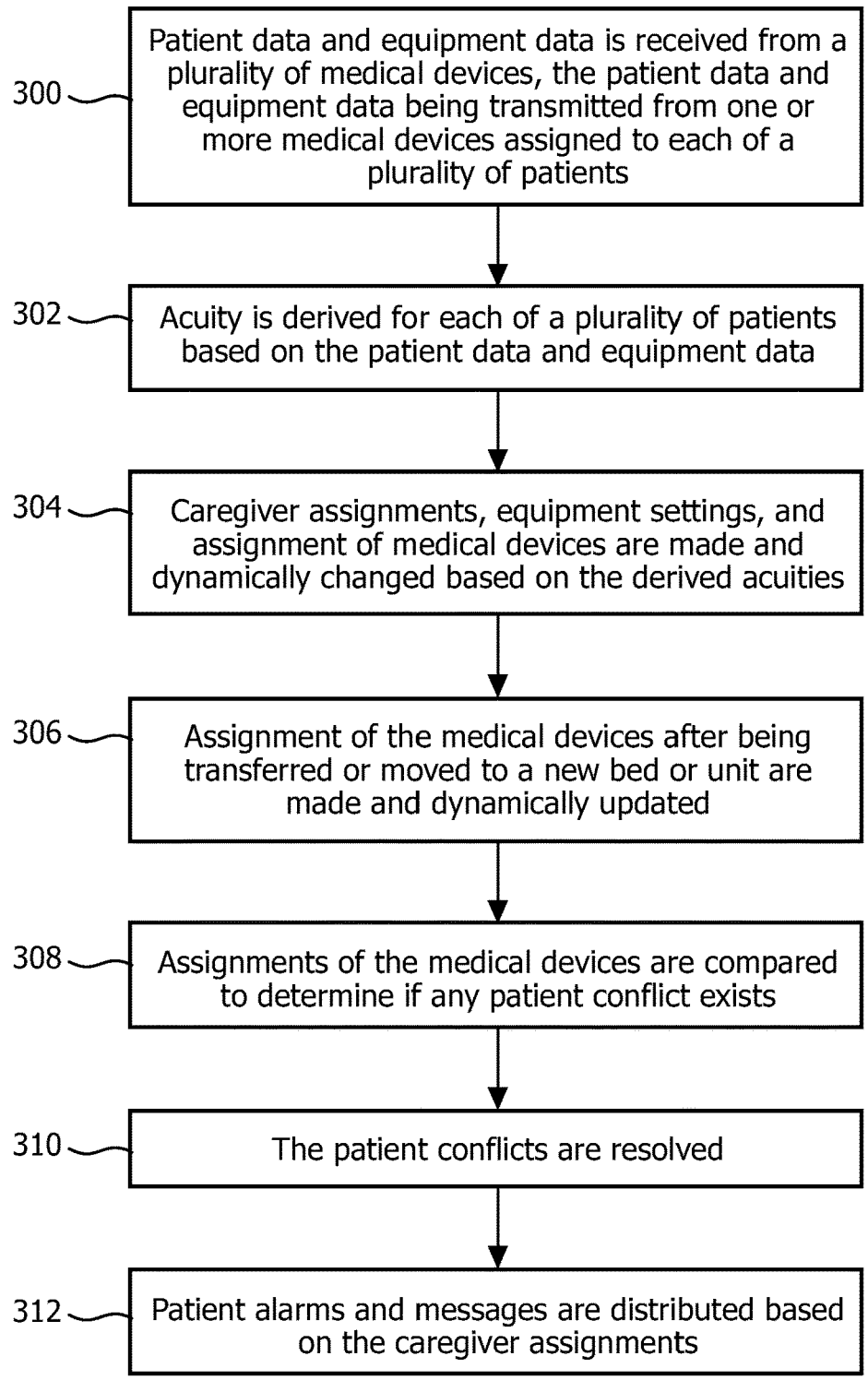
FIG. 4 is a flowchart diagram of the operation of the monitoring system in accordance with the present application.

FIG. 3 illustrates a user interface 200 of the administration management unit 40 associated with the administration manager 32 of the central or distributed monitoring station 12. The administration manager user interface 200 displays the assignment of the patients to various caregivers. The user interface 200 includes a caregiver sector 202 that identifies the available caregivers 204 for a given shift, communication devices 206 for each of the caregivers, and the caregiver roles 208 such as care tech, nurse, CDS nurse, charge nurse, and the like. The user interface 200 also includes a bed assignment sector 210 which indicates the different beds 212, the patients assigned to the beds 214, and the nurse assigned to the patients 216. A quality statistic summary sector 218 indicates the caregiver quality by indicating the number of patients 220, the number of assigned caregivers 222, the average early warning score (EWS) score 224, and the number of alert conditions or events 226. The user interface 200 also includes a paging or communication sector 228 to communicate with the difference caregivers. A EWS column 230 of the user interface 200 indicates the current CDS status of the patient. The user interface 200 also includes a sector on the quality statistics of the complete unit 232. A Reactivate EWS Deterioration Detection sector 234 allows to reactive the CDS EWS deterioration algorithm for a new or automatically assigned caregiver FIG. 4 illustrates the core operation of the controller of the central or distributed monitoring system. In a step 300, patient data and equipment data is received from a plurality of medical devices, the patient data and equipment data being transmitted from one or more medical devices assigned to each of a plurality of patients. In a step 302, an acuity is derived for each of a plurality of patients based on the patient data and equipment data. In a step 304, caregiver assignments, equipment settings, and assignment of medical devices are made and dynamically changed based on the derived acuities. In step 306, the assignment of the medical devices after being transferred or moved to a new bed or unit are made and dynamically updated. In a step 308, the assignments of the medical devices are compared to determine if any patient conflict exists. In a step 310, the patient conflicts are resolved. In a step 312, patient alarms and messages are distributed based on the caregiver assignments.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A method for managing medical devices and caregivers, the method implemented using one or more processors and comprising:
receiving, over one or more computing networks, from a plurality of medical devices currently assigned to a plurality of non-discharged patients, patient data and medical device data, wherein the patient data is indicative of physiological conditions of the plurality of patients and the medical device data includes a count of the plurality of medical devices assigned to each of the plurality of patients and types of the plurality of medical devices assigned to each of the plurality of patients;
deriving, based on the patient data and medical device data, an acuity for each given patient of the plurality of patients, wherein the acuity of the given patient is derived based on the types of the plurality of medical devices assigned to the given patient and the count of the plurality of medical devices assigned to the given patient, wherein a greater count corresponds to a greater acuity, and wherein at least a first type of medical device assigned to the given patient has a greater influence on the acuity of the given patient than a second type of medical device assigned to the given patient;
evaluating subsequent physiological data from the plurality of patients to detect a change in the derived acuity of one or more of the plurality of patients;
based on the detected change in the derived acuity of the one or more of the plurality of patients, dynamically changing an assignment of caregivers to the plurality of patients;
displaying, on one or more display devices, data indicative of the dynamically changed assignment of caregivers to the plurality of patients;
in response to a determination, made based on the evaluating, that a derived acuity of a first patient of the plurality of patients has increased dynamically altering medical device settings of one or more of the plurality of medical devices assigned to the first patient to increase an intensity of monitoring or treatment of the first patient; and
in response to a determination, made based on the evaluating, that a derived acuity of a second patient of the plurality of patients has decreased, dynamically altering medical device settings of one or more of the plurality of medical devices assigned to the second patient to decrease an intensity of monitoring or treatment provided to the second patient.

2. The method of claim 1, wherein the patient data includes at least one of physiological data, patient alarms or events, Clinical Decision System advisories and the physiological state of the patient.

3. The method of claim 1, wherein the dynamic changing of caregiver assignments is further based on at least one of: qualifications of available caregivers, a number of available beds, a current utilization of the beds, and existing responsibilities of the caregivers.

4. The method of claim 1, wherein one of the plurality of medical devices includes a patient transport device configured to transport a patient from a first care unit to a second care unit, the medical device data received from the transport device including an identifier of a particular patient to whom the transport device is assigned and location information, the method further including:
at the second care unit, replacing at least one of the medical devices assigned to the particular patient,
making and dynamically updating the assignment of the medical devices after the particular patient is transferred or moved to the second care unit; and
generating a message to return the at least one replaced device to the first care unit.

5. The method of claim 1, wherein the medical device data includes patient assignment information identifying the patient of the plurality of patients to whom it is assigned and further including:
comparing the patient assignment information in the medical device data to determine if any of the medical devices is assigned to more than one patient; and
unassigning a previously assigned patient such that the medical device data removes the patient assignment information of a previous patient.

6. The method of claim 1, wherein the medical device data includes, for each medical device of the plurality of medical devices, a location and destination of the medical device, an identification of the medical device, a patient assignment of the medical device, a usage of the medical device, and a state of the medical device.

7. The method of claim 1, wherein the patient data includes, for each of the plurality of patients, at least one of physiological data, patient alarms or events, and a physiological state of the patient.

8. The method of claim 7, wherein evaluating the subsequent physiological data includes evaluating the patient data for the physiological data approaching a physiological data threshold, a trend of the physiological data approaching a trend threshold, unstable physiological values, and combinations of the physiological data approaching a combination of thresholds.

9. The method of claim 1, further including:
storing the caregiver assignments and equipment assignments in a memory;
receiving input of nosocomial infections acquired by patients and former patients, and
tracking equipment and caregivers assigned to the patients and former patients that acquired the nosocomial infections.

10. At least one non-transitory computer-readable medium comprising instructions that, in response to execution of the instructions by one or more processors, cause the one or more processors to perform the following operations:
receiving, over one or more computing networks, from a plurality of medical devices currently assigned to a plurality of non-discharged patients, patient data and medical device data, wherein the patient data is indicative of physiological conditions of the plurality of patients and the medical device data includes a count of the plurality of medical devices assigned to each of the plurality of patients and types of the plurality of medical devices assigned to each of the plurality of patients;
deriving, based on the patient data and medical device data, an acuity for each given patient of the plurality of patients, wherein the acuity of the given patient is derived based on the types of the plurality of medical devices assigned to the given patient and the count of the plurality of medical devices assigned to the given patient, wherein a greater count corresponds to a greater acuity, and wherein at least a first type of medical device assigned to the given patient has a greater influence on the acuity of the given patient than a second type of medical device assigned to the given patient;

evaluating subsequent physiological data from the plurality of patients to detect a change in the derived acuity of one or more of the plurality of patients;

based on the detected change in the derived acuity of the one or more of the plurality of patients, dynamically changing an assignment of caregivers to the plurality of patients;

displaying, on one or more display devices, data indicative of the dynamically changed assignment of caregivers to the plurality of patients;

in response to a determination, made based on the evaluating, that a derived acuity of a first patient of the plurality of patients has increased dynamically altering medical device settings of one or more of the plurality of medical devices assigned to the first patient to increase an intensity of monitoring or treatment of the first patient; and in response to a determination, made based on the evaluating, that a derived acuity of a second patient of the plurality of patients has decreased, dynamically altering medical device settings of one or more of the plurality of medical devices assigned to the second patient to decrease an intensity of monitoring or treatment provided to the second patient.

11. The at least one non-transitory computer-readable medium of claim 10, wherein the patient data includes at least one of physiological data, patient alarms or events, Clinical Decision System advisories and the physiological state of the patient.

12. The at least one non-transitory computer-readable medium of claim 10, wherein the dynamic changing of caregiver assignments is further based on at least one of: qualifications of available caregivers, a number of available beds, a current utilization of the beds, and existing responsibilities of the caregivers.

13. The at least one non-transitory computer-readable medium of claim 10, wherein one of the plurality of medical devices includes a patient transport device configured to transport a patient from a first care unit to a second care unit, the medical device data received from the transport device including an identifier of a particular patient to whom the transport device is assigned and location information, and further comprising instructions for:
at the second care unit, replacing at least one of the medical devices assigned to the particular patient,
making and dynamically updating the assignment of the medical devices after the particular patient is transferred or moved to the second care unit; and
generating a message to return the at least one replaced device to the first care unit.

14. The at least one non-transitory computer-readable medium of claim 10, wherein the medical device data includes patient assignment information identifying the patient of the plurality of patients to whom it is assigned and further comprising instructions for:
comparing the patient assignment information in the medical device data to determine if any of the medical devices is assigned to more than one patient; and
unassigning a previously assigned patient such that the medical device data removes the patient assignment information of a previous patient.

15. The at least one non-transitory computer-readable medium of claim 10, wherein the medical device data includes, for each medical device of the plurality of medical devices, a location and destination of the medical device, an identification of the medical device, a patient assignment of the medical device, a usage of the medical device, and a state of the medical device.

16. The at least one non-transitory computer-readable medium of claim 10, wherein the patient data includes, for each of the plurality of patients, at least one of physiological data, patient alarms or events, and a physiological state of the patient.

17. The at least one non-transitory computer-readable medium of claim 16, wherein evaluating the subsequent physiological data includes evaluating the patient data for the physiological data approaching a physiological data threshold, a trend of the physiological data approaching a trend threshold, unstable physiological values, and combinations of the physiological data approaching a combination of thresholds.

18. The at least one non-transitory computer-readable medium of claim 10, further including instructions for:
storing the caregiver assignments and equipment assignments in a memory;
receiving input of nosocomial infections acquired by patients and former patients, and
tracking equipment and caregivers assigned to the patients and former patients that acquired the nosocomial infections.

19. A system comprising one or more processors and memory operably coupled with the one or more processors, wherein the memory stores instructions that, in response to execution of the instructions by one or more processors, cause the one or more processors to perform the following operations:
receiving, over one or more computing networks, from a plurality of medical devices currently assigned to a plurality of non-discharged patients, patient data and medical device data, wherein the patient data is indicative of physiological conditions of the plurality of patients and the medical device data includes a count of the plurality of medical devices assigned to each of the plurality of patients and types of the plurality of medical devices assigned to each of the plurality of patients;
deriving, based on the patient data and medical device data, an acuity for each given patient of the plurality of patients, wherein the acuity of the given patient is derived based on the types of the plurality of medical devices assigned to the given patient and the count of the plurality of medical devices assigned to the given patient, wherein a greater count corresponds to a greater acuity, and wherein at least a first type of medical device assigned to the given patient has a greater influence on the acuity of the given patient than a second type of medical device assigned to the given patient;
evaluating subsequent physiological data from the plurality of patients to detect a change in the derived acuity of one or more of the plurality of patients;
based on the detected change in the derived acuity of the one or more of the plurality of patients, dynamically changing an assignment of caregivers to the plurality of patients;

displaying, on one or more display devices, data indicative of the dynamically changed assignment of caregivers to the plurality of patients;

in response to a determination, made based on the evaluating, that a derived acuity of a first patient of the plurality of patients has increased dynamically altering medical device settings of one or more of the plurality of medical devices assigned to the first patient to increase an intensity of monitoring or treatment of the first patient; and in response to a determination, made based on the evaluating, that a derived acuity of a second patient of the plurality of patients has decreased, dynamically altering medical device settings of one or more of the plurality of medical devices assigned to the second patient to decrease an intensity of monitoring or treatment provided to the second patient.

* * * * *